(12) United States Patent
Furumori et al.

(10) Patent No.: US 6,356,621 B1
(45) Date of Patent: Mar. 12, 2002

(54) PRESSURE-SENSITIVE ADHESIVE SHEET FOR RADIOGRAPHY

(75) Inventors: Kenji Furumori; Takamasa Kuroya; Toshiyuki Yoshikawa, all of Osaka (JP)

(73) Assignee: Nitto Denko Corporation, Osaka (JP)

(*) Notice: Subject to any disclaimer, the term of this patent is extended or adjusted under 35 U.S.C. 154(b) by 0 days.

(21) Appl. No.: 09/545,296

(22) Filed: Apr. 7, 2000

(30) Foreign Application Priority Data

Jul. 14, 1999 (JP) .......... 11-005248
Jul. 14, 1999 (JP) .......... 11-199987

(51) Int. Cl.[7] ............................ G01B 3/00
(52) U.S. Cl. ............ 378/162; 378/163; 378/164; 378/207
(58) Field of Search ............. 378/162, 163, 378/164, 207

(56) References Cited

U.S. PATENT DOCUMENTS

| | | | |
|---|---|---|---|
| 2,650,308 A | * 8/1953 | Catlin | 378/163 |
| 4,506,676 A | * 3/1985 | Duska | 378/163 |
| 4,860,331 A | * 8/1989 | Williams et al. | 378/163 |
| 5,193,106 A | * 3/1993 | DeSena | 378/163 |
| 5,216,700 A | * 6/1993 | Cherian | 378/163 |
| 6,198,807 B1 | * 3/2001 | DeSena | 378/162 |

FOREIGN PATENT DOCUMENTS

| | | | |
|---|---|---|---|
| JP | 08056983 A | 3/1996 | ... A61F/13/02 |
| JP | 10-290797 | 4/1998 | |
| WO | WO 96/01096 | 1/1996 | |

* cited by examiner

*Primary Examiner*—Drew Dunn
(74) *Attorney, Agent, or Firm*—Kilyk & Bowersox, PLLC

(57) ABSTRACT

A pressure-sensitive adhesive sheet comprising a plastic sheet having on one surface thereof a pressure-sensitive adhesive layer, wherein the plastic sheet has on at least one surface thereof a print layer having a thickness of 40 to 1,000 μm and containing 30 to 90% by weight based on the total weight of the print layer of an X-ray absorbing metal. The print pattern may be scales, grid lines, numbers, etc. singly or in combination. Information on individual subject or scales or grid lines pattern may be copied in a radiograph having an image of the inside of the subject body. This enables surgeons to determine the size of the inside of the subject body or position of target organ with ease.

20 Claims, 2 Drawing Sheets

PRESSURE-SENSITIVE ADHESIVE SHEET FOR RADIOGRAPHY

BACKGROUND OF THE INVENTION

1. Field of the Invention

The present invention relates to a pressure-sensitive adhesive sheet, in particular to a pressure-sensitive adhesive sheet for use in radiography. More particularly, the present invention relates to a pressure-sensitive adhesive sheet that allows incorporation of particular information on a subject into radiograph or reproducing a scale or grid pattern in a radiograph that has taken a picture of the inside of the body of a subject so that the size of the inside of the body or the position of the organs of the subject can be determined with ease in a simple manner.

2. Description of the Related Art

Hitherto, to aid medicine, a ruler is used in order to determine the position of puncture when injection is to be performed or the position of the site where operation is to be practiced. In particular, when organs inside the body of a subject is targeted, the determination of position of puncture or of the site where operation is to be practiced by applying a ruler onto the radiograph. More particularly, after radiography, a ruler is applied to the obtained radiograph. The distance between the marked place to the target place is measured on the skin of the patient, and then the position of puncture or operation site is marked with an oil-base ink, for example, so that the position of puncture or operation site can be determined.

The determination of position with a ruler has the problems that bringing and using rulers is troublesome and that accurate measurement is difficult for bent portions. Further, generally the radiograph and the object radiographed are not in an equi-powered relationship (i.e., not at the same magnification or reduction ratio) to each other, i.e., either high-powered (magnified) or low-powered (reduced), so that accurate measurement of the positions is difficult if a ruler is used on the obtained radiograph.

Also, image processing of a radiograph image on a computer has been performed in order to make an accurate measurement of the size of organs, etc. However, introduction of image processing apparatus incurs much cost so that the introduction of such an apparatus is not realistic for surgery or small-sized hospitals.

On the other hand, JP-A-8-56983 (1996) discloses a medical pressure-sensitive adhesive tape whose tape is provided with a scale. Use of the pressure-sensitive adhesive sheet obviates the trouble of its bringing or use and facilitates measurements of bent portions.

However, use of such a medical pressure-sensitive adhesive tape is contemplated upon observation of the state of disease using a camera or video camera. Hence, like the use of a ruler, it is difficult with such a tape to determine the position of an organ or the like in the body of a subject with accuracy.

SUMMARY OF THE INVENTION

In view of the above, an object of the present invention is to provide a pressure-sensitive adhesive sheet for radiography that allows easy and accurate determination of information on the position of puncture or operation site in the inside of the body of a subject or information on the subject from a radiograph obtained using it.

The present inventors have made intensive research with view to achieving the above object and as a result they have found that use of a pressure-sensitive adhesive sheet including a plastic sheet having formed on at least one surface thereof a print layer containing an X-ray absorbing metal and a pressure-sensitive adhesive layer on either one of the surfaces of the resulting plastic sheet in radiography enables one to determine the position of puncture or operation site in the inside of the body of the subject easily and accurately. The present invention has been achieved based on this discovery.

Accordingly, a pressure-sensitive adhesive sheet comprising a plastic sheet having on one surface thereof a pressure-sensitive adhesive layer, wherein the plastic sheet has on at least one surface thereof a print layer having a thickness of 40 to 1,000 $\mu$m and containing 30 to 90% by weight based on the total weight of the print layer of an X-ray absorbing metal.

Here, the pressure-sensitive adhesive layer may be provided on the print layer.

The pressure-sensitive adhesive layer may be provided on a surface of the plastic sheet opposite to a side where the print layer is provided and wherein a light-transmitting layer is provided on the print layer.

Preferably, the X-ray absorbing metal has a density of 8,000 kg/m$^3$.

The X-ray absorbing metal is preferably tungsten.

The print layer may be in the form of a scale pattern or grid pattern.

The scale pattern may be a numerical value scale for the measurement of lengths.

The pressure-sensitive adhesive sheet may have an arcuate end in its longitudinal direction.

The pressure-sensitive adhesive sheet may further comprise a release liner on a surface of which the pressure-sensitive adhesive sheet is applied.

The release liner may be provided with a slit for division.

In the present invention, a print layer is provided on one surface of a plastic sheet. The print layer contains an X-ray absorbing metal such as tungsten in an amount of 30 to 90% by weight based on the total weight thereof and has a thickness of 40 to 1,000 $\mu$m. The print layer may be provided in the form of a scale or grid line or the like pattern and in this case, radiography using the pressure-sensitive adhesive sheet of the present invention can reproduce the printed pattern in the obtained radiograph sharply. This offers advantages that the size of the inside of the body of a subject or accurate position of a target organ can be grasped easily so that appropriate medical treatments can be offered.

The above and other objects, effects, features and advantages of the present invention will become more apparent from the following description of preferred embodiments.

DETAILED DESCRIPTION OF THE INVENTION

Figure 1:
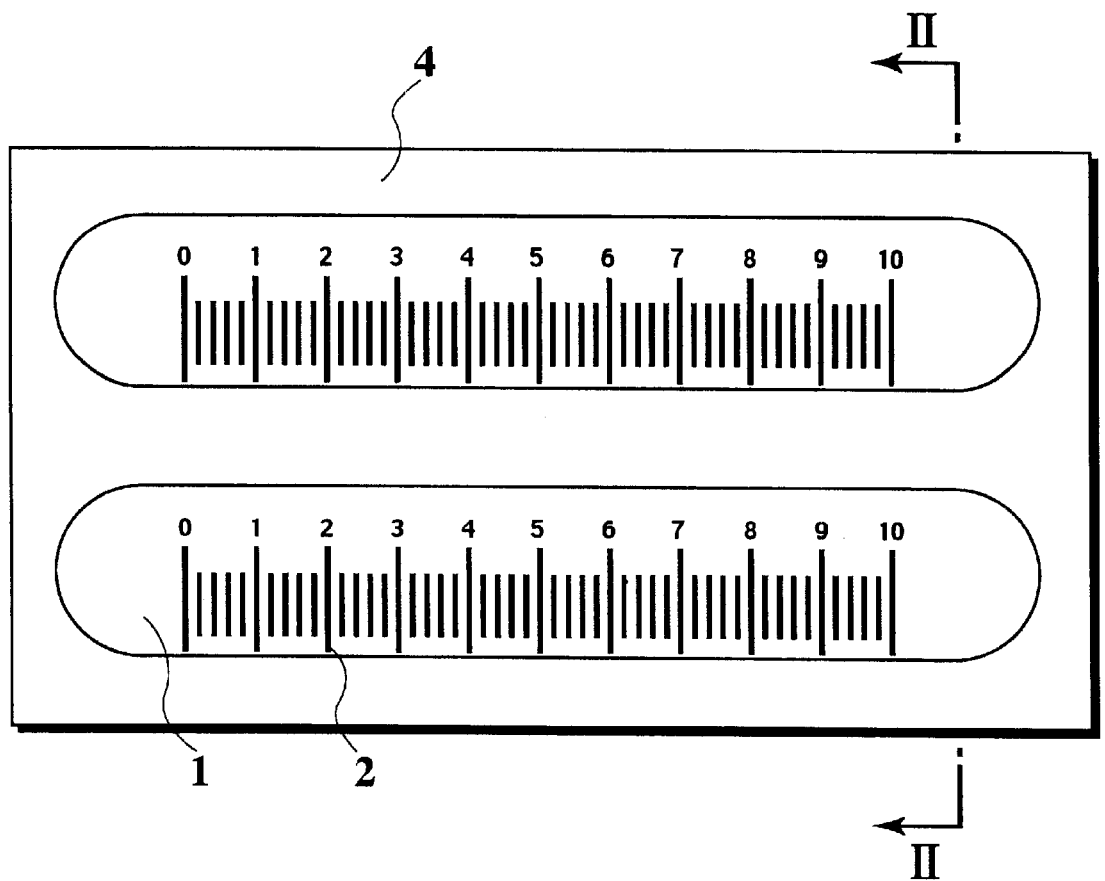
FIG. 1 is a plan view showing an example of a pressure-sensitive adhesive sheet for radiography with a scale in accordance with the present invention.

The pressure-sensitive adhesive sheet for radiography (hereafter, sometimes simply referred to as "pressure-sensitive sheet") of the present invention comprises a plastic sheet 1, on one surface of which is formed a print layer 2. A pressure-sensitive adhesive layer 3 is formed on either one of the surfaces of the resulting plastic sheet 1 with the print layer 2. The plastic sheet 1 is not particularly limited so far as it is transparent to the X-ray used and has a surface that permits printing thereon. Specifically, examples of plastic that can be used in the plastic sheet comprise polyesters, polypropylenes, polyethylenes, polyurethanes, polyvinyl chlorides, ethylene/vinyl acetate copolymers, ethylene/methyl methacrylate copolymers, silicone resins, acrylic resins, polycarbonates, polyimides, etc. When a scale or grid line is to be printed, it is necessary to use nonelastic materials such as polyesters, acrylic resins, polycarbonate resins, polyimides, etc.

In the case where the plastic sheet must be flexible, desirably it has a thickness of 10 to 100 $\mu$m, preferably 15 to 50 $\mu$m. When it does not have to be flexible, it may have a thickness of up to 500 $\mu$m. One or both ends of the plastic sheet in the longitudinal direction may be rounded so that an arcuate end or ends are formed.

In the pressure-sensitive adhesive sheet for radiography of the present invention, the print layer absorbs X-ray irradiated thereto while the plastic sheet portion must be transparent to the X-ray. It is preferred that the plastic sheet have an X-ray transmission of 95% or higher in order for the image on the printed layer to be sharply reproduced on a radiograph. The above value is a rough indication since the radiation dose (intensity) will vary radiation site to radiation site in the body of a subject.

Furthermore, it is desirable that the pressure-sensitive adhesive sheet for radiography of the present invention has a 10% modulus of 0.5 kgf/12 mm or more, preferably 1 kgf/12 mm or more in order to assure accuracy in printing a scale or grid line.

In the pressure-sensitive adhesive sheet of the present invention, the print layer 2 is provided on at least one surface of the plastic sheet 1. The print layer 2 contains an X-ray absorbing metal; absorption of X-ray in the print layer 2 results in sharp reproduction of the printed pattern on a radiograph. As the X-ray absorbing metal having such an effect, mention may be made of those metals having low X-ray transmission at a typical emission line wavelength (1, 1.3, or 1.5 angstroms (100, 130, or 150 nm)) of tungsten target X-ray tube generally used for medical X-ray. Preferred examples thereof include, for example, tungsten, tantalum, platinum, gold, silver, etc. These metals are high-density metals having a density of 8,000 kg/m$^2$ or higher and exhibit excellent effects in X-ray absorption efficiency and safety. Of these, it is preferred to use tungsten from the economical viewpoint.

The print layer used in the present invention contains a binder resin as well as the above metal and is mixed with a diluent solvent, if needed, before it is subjected to the printing step. In other words, the above X-ray absorbing metal must be pulverized into fine powder before it can be added to the binder resin in order to give proper viscosity and fluidity. Thus, the average particle diameter of the metal fine powder is preferably on the order of 0.05 to 5 $\mu$m.

The binder resin that is necessary at the time of forming the above print layer has to be selected so as to comply with various printing methods such as gravure printing, flexographic printing, sealing printing, and screen printing, and thermal transfer printing. Since the present invention is not limited to a specific printing method, a binder resin suitable for the adopted printing method may be selected.

As examples of such a binder resin, mention may be made of, for example, acrylic resins, polyesters, urethanes, rubber-based resins, phenol-based resins, epoxy-based resins, silicone-based resins, wax-based resins, etc., which can be used advantageously from the viewpoint of imparting the print layer with follow-up property along an uneven surface of a subject or flexibility to bending.

In the pressure-sensitive adhesive sheet of the present invention, the image printed as the printed layer on the plastic sheet must be recognized sharply as a configuration on the screen of an X-ray monitoring apparatus upon X-ray observation or on radiograph. Accordingly, the thickness of the print layer to be formed is an important factor. In the present invention, the coat thickness for the print layer is 40 to 1,000 $\mu$m, preferably 70 to 500 $\mu$m. If the coat thickness is below 40 $\mu$m, no sharp image can be obtained. On the other hand, in the case of the coat thickness of above 1,000 $\mu$m, a sharp image can be obtained but the flexibility of sheet itself tends to be decreased so that the resulting sheet does not fit for the applications of the pressure-sensitive adhesive sheet of the present invention.

In order for the image of the print layer to be sharply recognized as a configuration on a radiograph, it is empirically known that the print layer has an X-ray transmission of 20% or lower. In the present invention, the content of X-ray absorbing metal in the print layer is adjusted to a value in the range of 30 to 90% by weight, preferably 50 to 90% by weight. If the metal content is below 30% by weight, the X-ray transmission cannot be decreased sufficiently depending on the kind of metal, so that it is difficult to obtain a sharp image that can be recognized visually. On the other hand, if the metal content exceeds 90% by weight, the print layer tends to become so brittle that there is the fear that falling of the print layer will occur during its production process or use.

In the present invention, upon forming a print layer as described above, the metal is pulverized to fine powder before it is mixed with the binder resin to form an ink for printing. In this case, if the viscosity of the ink is low, immediate sedimentation of the metal powder in the ink will occur during a printing process due to the very high density of the metal powder. Although it is desirable that the ink have high viscosity, high viscosity tends to cause slight touching, so that it is generally adopted that the viscosity of ink is adjusted by use of a diluent solvent adapted for a particular binder resin. What is preferred as such a diluent includes butyl cellosolve, cyclohexanone, aromatic hydrocarbon solvents, ketone solvents, polyhydric alcohol solvents, etc.

Further, the pressure-sensitive adhesive sheet of the present invention includes a print layer on one or both surfaces of the plastic sheet. The image to be printed on the plastic sheet is not particularly limited and any image or pattern may be printed depending on the purpose. For example, information on an individual (for example, age, sex, blood group, etc.) or scales or grid lines for the measurement of sizes may be printed. For general-purpose applications, it is preferred that scales or grid lines for the measurement of accurate position of operation site in the inside of the body of a subject be printed.

In the case where scales or grid lines are printed as the image, their shape or distance between adjacent images is not limited particularly. For example, straight-line scales with divisions of 1 mm to several millimeters, circular or grid scales at a distance of several millimeters may be used. Two or more of these may be arranged in combination in various fashions. The above scales may be provided with numbers.

In the pressure-sensitive adhesive sheet according to one embodiment of the present invention, the print layer is formed on one surface of the plastic sheet and the print images (patterns) are scale patterns as illustrated in FIG. 1. More specifically, it is preferred that the pattern be scales of numerical values or grid lines such as square grid lines for the measurement of lengths. In the case of numerical value scales, for example, shorter line segments at a pitch of 2 mm from each other may be printed as shown in FIG. 1 and further longer line segments at a pitch of 1 cm from each other may be printed. Naturally, the minimum pitch may be set to 1 mm. However, the minimum division (pitch) is preferably 2 mm in order to allow depicting more or less thicker line segments to thereby sharply copy or reproduce the scale pattern on the radiograph without overlaps of the line segments or scale pattern. If desired, information on an individual subject may be printed.

Figure 2:
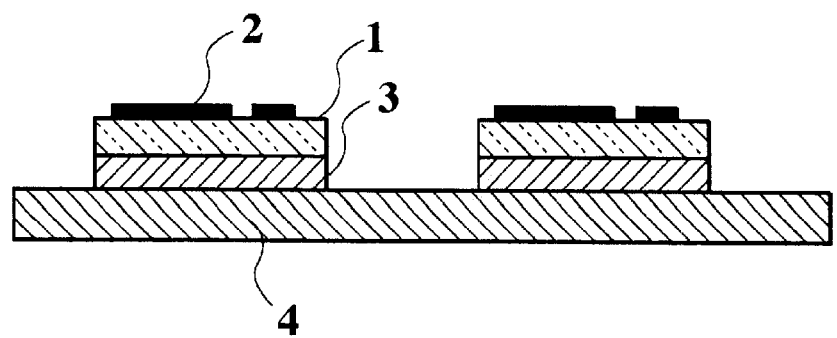
FIG. 2 is a cross-sectional view of the pressure-sensitive adhesive sheet shown in FIG. 1 along the line II—II.
Figure 3:
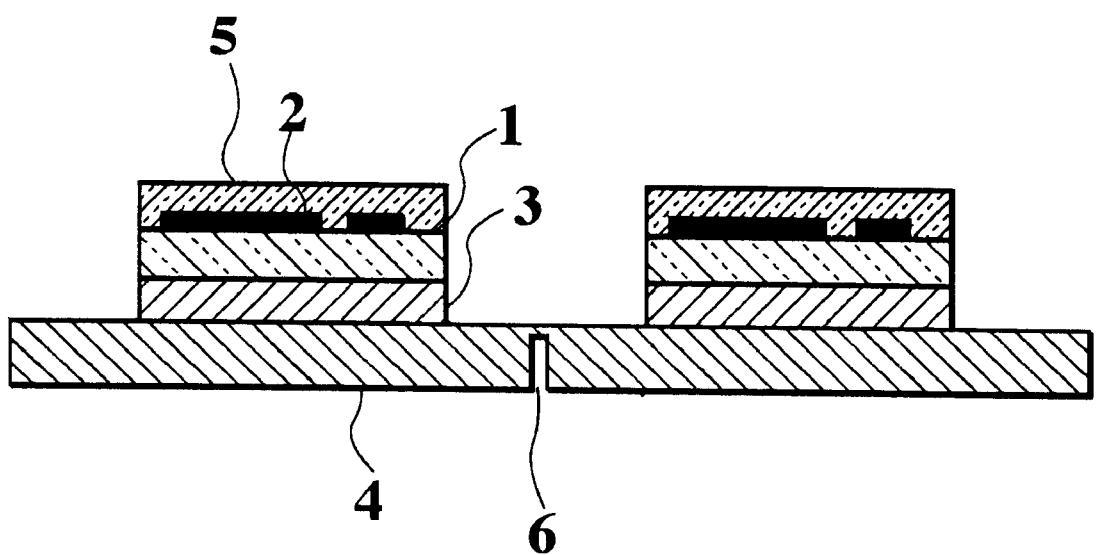
FIG. 3 is a cross-sectional view of another example of the pressure-sensitive adhesive sheet for radiography with a scale in accordance with the present invention.

The pressure-sensitive adhesive sheet for radiography of the present invention is provided with a pressure-sensitive adhesive layer 3. The pressure-sensitive adhesive layer 3 may be provided on the print layer 2 so that it can cover the print layer 2 or on the surface of the plastic sheet 1 opposite to the surface where the print layer 2 is provided. In the latter case, it is preferred that a light-transmitting resin layer 5 be formed on the print layer 2 as shown in FIG. 3 in order to protect the print layer 2 and prevent it from falling off from the plastic sheet 1. A release liner 4 may be laminated on the exposed surface of the pressure-sensitive adhesive layer 3 until the pressure-sensitive adhesive sheet is used, if desired, to protect the pressure-sensitive adhesive layer. The release liner 4 is preferably provided with one or more slits 6 for dividing it in order to improve the operability of release upon use. Furthermore, a plurality of pressure-sensitive adhesive sheets of the present invention may be provided with respective release liners 4 on their respective surfaces of the pressure-sensitive adhesive layer 3. Alternatively, from the economical viewpoint, it is preferred that a plurality of pressure-sensitive sheets be mounted on one release liner 4 as shown in FIGS. 1 to 3. Note that the pressure-sensitive adhesive sheet of the present invention may be formed as a long sheet. This allows the sheet to be wound in the form of a roll. In this case, release treatment of the back surface of the pressure-sensitive adhesive sheet (on which the pressure-sensitive adhesive layer 3 contacts) can omit use of the release liner 4.

The above pressure-sensitive adhesive layer 3 is coated to a thickness of 5 to 100 $\mu$m, preferably 10 to 50 $\mu$m from the viewpoints of fixation and economy.

The pressure-sensitive adhesive that constitutes the pressure-sensitive adhesive layer may be those generally used for pressure-sensitive sheets, such as rubber-based pressure-sensitive adhesives, acrylic based pressure-sensitive adhesives, and vinyl ether-based pressure-sensitive adhesives. For other additives such as a tackifier may be those generally used. It is preferred that those additives whose safety has been already determined be used.

As described above, in the case where the surface of the print layer is covered with a light-transmitting resin layer, the resin like the above plastic sheet must be transparent to X-rays. The light-transmitting resin that can be used is not limited particularly and more specifically, it may be the materials exemplified for the above plastic sheet. The light-transmitting resin layer may be a laminate of sheet-like materials or it may be formed by coating a solution of the resin on the print layer so far as the solution does not dissolve the print layer. Since the light-transmitting resin layer to be formed is contemplated to protect the print layer, it does not have so much thick and it is sufficient for it to have a thickness of 1,000 $\mu$m or less, preferably 5 to 200 $\mu$m, more preferably 3 to 20 $\mu$m.

As a method for using the pressure-sensitive adhesive sheet for radiography of the present invention may include the following examples, for example. The pressure-sensitive adhesive sheet of the present invention is applied to a subject body on which radiography is to be performed and then radiography is practiced. As a result, the image of the print layer appears as a clear configuration on an X-ray monitor or on a radiograph. This assures accurate determination of the position of operation site in the inside of the subject body. Thus, the pressure-sensitive adhesive sheet of the present invention can be used in every field of art where radiography is involved.

The shape of the pressure-sensitive adhesive sheet of the present invention is not particularly limited but may be configured so as to comply with the size or form of the subject to which it is applied. It may be in the form of a tape. Furthermore, the pressure-sensitive adhesive sheet may be subjected to sterilization treatment by irradiating γ-rays, electron beam, plasma or the like or to sterilization treatment with ethylene oxide gas or steam.

When the pressure-sensitive adhesive sheet of the present invention, for example, a sheet with scale prints, is applied to a human body and radiography is practiced, the scale absorbs the X-ray used and is opaque thereto so that the developed radiograph contains recorded therein a scale corresponding to the original scale at the same reduction or magnification ratio as that of the radiograph. This scale can be used for determining the position of bones or organs in the inside of the human body with accuracy and with ease.

EXAMPLES

Hereinafter, the present invention will be explained in detail by examples. However, the present invention should not be construed as being limited thereto. All the parts are by weight unless otherwise indicated specifically.

Example 1

Under inert gas (nitrogen gas) atmosphere at a pressure of 1 atom, 10 parts of 2-hydroxyethyl acrylate and 90 parts of 2-ethylhexyl acrylate were copolymerized in ethyl acetate at 60° C. for 8 hours to form a solution of an acrylate ester-based pressure-sensitive adhesive.

The pressure-sensitive adhesive solution was coated on one surface of a polyethylene terephthalate sheet (38 $\mu$m thick) and coated to form a 30-$\mu$m thick pressure-sensitive adhesive layer. On the surface of the pressure-sensitive adhesive layer was laminated a release liner to fabricate a pressure-sensitive adhesive sheet.

The thus-obtained pressure-sensitive adhesive sheet is provided on the back surface of its polyethylene terephthalate sheet with a print layer of 100-$\mu$m thick by silk screen printing with a printing ink that comprises a polyester-based resin as a binder resin, containing 65% by weight of tungsten having a particle diameter of 0.6 $\mu$m. The print pattern was a straight-line scale at a pitch of 2 mm.

Then, a polyester resin was laminated by coating it on a surface of the formed print layer to a thickness of 10 $\mu$m on dry basis to fabricate a pressure-sensitive adhesive sheet (with scales) for radiograph of the present invention.

Comparative Example 1

A pressure-sensitive adhesive sheet for radiograph was fabricated in the same manner as in Example 1 except that the print ink was coated to a thickness of 30 $\mu$m on dry basis.

Comparative Example 2

A pressure-sensitive adhesive sheet for radiograph was fabricated in the same manner as in Example 1 except that the X-ray absorbing metal was replaced by barium sulfate.

Comparative Example 3

A pressure-sensitive adhesive sheet for radiograph was fabricated in the same manner as in Example 1 except that the amount of tungsten in the print ink was 25% by weight.

The scaled pressure-sensitive adhesive sheets of Example 1 and Comparative Examples 1 to 3 above were used in radiography and degree of whitening of each sample was evaluated. Table 1 shows the results.

Radiography

<Buccal Method>

Radiography was performed by a buccal method used as a general technique in the field of dentistry. On a surface of a polyvinyl chloride bag for a 3 cm×3 cm X-ray film for the buccal method was attached each of the scaled pressure-sensitive adhesive sheet fabricated in Example 1 and Comparative Examples 1 to 3. The film bag was fixed to the position of a tooth by the finger of the subject and X-ray was irradiated from outside the oral cavity to take a picture of the tooth.

Using the obtained radiographs, evaluation was made according to the following criteria.

A: The scale of the pressure-sensitive adhesive sheet on the radiograph could be clearly recognized even where it overlapped the tooth.

B: The scale of the pressure-sensitive adhesive sheet on the radiograph could be recognized only slightly where it overlapped the tooth.

C: The scale of the pressure-sensitive adhesive sheet on the radiograph was illegible where it overlapped the tooth.

<Panoramic Shooting>

Radiography was performed by a panoramic shooting method generally used in the field of dentistry. Each of the scaled pressure-sensitive adhesive sheets fabricated in Example 1 and Comparative Examples 1 to 3 was applied to the facial skin of the subject and X-rays were irradiated to perform radiography.

The same criteria for evaluation as those for the buccal method described above were used for the panoramic shooting method.

TABLE 1

|  | Buccal method | Panoramic method |
|---|---|---|
| Example 1 | A | A |
| Comparative Example 1 | C | C |
| Comparative Example 2 | C | C |
| Comparative Example 3 | B | C |

The invention may be embodied in other specific forms without departing from the spirit or essential characteristics thereof. Therefore, the present embodiment is to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A pressure-sensitive adhesive sheet comprising a plastic sheet having on one surface thereof a pressure-sensitive adhesive layer, wherein the plastic sheet has on at least one surface thereof a print layer having a thickness of 40 to 1,000 μm and containing 30 to 90% by weight based on the total weight of the print layer of an X-ray absorbing metal.

2. The pressure-sensitive adhesive sheet as claimed in claim 1, wherein the pressure-sensitive adhesive layer is provided on the print layer.

3. The pressure-sensitive adhesive sheet as claimed in claim 1, wherein the pressure-sensitive adhesive layer is provided on a surface of the plastic sheet opposite to a side where the print layer is provided and wherein a light-transmitting layer is provided on the print layer.

4. The pressure-sensitive adhesive sheet as claimed in claim 1, wherein the X-ray absorbing metal has a density of 8,000 kg/m$^3$.

5. The pressure-sensitive adhesive sheet as claimed in claim 2, wherein the X-ray absorbing metal has a density of 8,000 kg/m$^3$.

6. The pressure-sensitive adhesive sheet as claimed in claim 3, wherein the X-ray absorbing metal has a density of 8,000 kg/m$^3$.

7. The pressure-sensitive adhesive sheet as claimed in claim 4, wherein the X-ray absorbing metal is tungsten.

8. The pressure-sensitive adhesive sheet as claimed in claim 5, wherein the X-ray absorbing metal is tungsten.

9. The pressure-sensitive adhesive sheet as claimed in claim 6, wherein the X-ray absorbing metal is tungsten.

10. The pressure-sensitive adhesive sheet as claimed in claim 1, wherein the print layer is in the form of a scale pattern or grid pattern.

11. The pressure-sensitive adhesive sheet as claimed in claim 10, wherein the scale pattern is a numerical value scale for the measurement of lengths.

12. The pressure-sensitive adhesive sheet as claimed in claim 1, wherein the pressure-sensitive adhesive sheet has an arcuate end in its longitudinal direction.

13. The pressure-sensitive adhesive sheet as claimed in claim 1, further comprising a release liner on a surface of which the pressure-sensitive adhesive sheet is applied.

14. The pressure-sensitive adhesive sheet as claimed in claim 13, wherein the release liner is provided with a slit for division.

15. The pressure-sensitive adhesive sheet as claimed in claim 13, wherein the pressure-sensitive adhesive layer is provided on the print layer.

16. The pressure-sensitive adhesive sheet as claimed in claim 13, wherein the pressure-sensitive adhesive layer is provided on a surface of the plastic sheet opposite to a side where the print layer is provided and wherein a light-transmitting layer is provided on the print layer.

17. The pressure-sensitive adhesive sheet as claimed in claim 13, wherein the X-ray absorbing metal has a density of 8,000 kg/m$^3$.

18. The pressure-sensitive adhesive sheet as claimed in claim 17, wherein the X-ray absorbing metal is tungsten.

19. The pressure-sensitive adhesive sheet as claimed in claim 13, wherein the print layer is in the form of a scale pattern or grid pattern.

20. The pressure-sensitive adhesive sheet as claimed in claim 13, wherein the pressure-sensitive adhesive sheet has an arcuate end in its longitudinal direction.

* * * * *